United States Patent [19]

Marchionna et al.

[11] Patent Number: 5,032,618
[45] Date of Patent: Jul. 16, 1991

[54] PROCESS FOR PRODUCING METHANOL FORM SYNTHESIS GAS, IN THE LIQUID PHASE

[75] Inventors: Mario Marchionna; Massimo Lami, both of Milan; Francesco Ancillotti, San Donato Milanese, all of Italy

[73] Assignee: Snamprogetti S.p.A., Milan, Italy

[21] Appl. No.: 455,007

[22] Filed: Dec. 22, 1989

[30] Foreign Application Priority Data

Dec. 23, 1988 [IT] Italy ............................... 23102 A/88
Nov. 10, 1989 [IT] Italy ............................... 22352 A/89

[51] Int. Cl.$^5$ .............................................. C07C 27/06
[52] U.S. Cl. ................................... 518/700; 502/156; 568/885
[58] Field of Search ....................... 518/780; 568/885

[56] References Cited

U.S. PATENT DOCUMENTS 4,731,386 3/1988 Onsager .............................. 518/700

FOREIGN PATENT DOCUMENTS 1175798 9/1984 Canada ................................. 518/700
809803 8/1951 Fed. Rep. of Germany ...... 518/700
860048 12/1982 Fed. Rep. of Germany ...... 518/700

*Primary Examiner*—Howard T. Mars
*Attorney, Agent, or Firm*—Oblon, Spivak, McClelland, Maier & Neustadt

[57] ABSTRACT

A process for producing methanol from synthesis gas in the liquid phase is disclosed, which comprises reacting CO with $H_2$ in the presence of a catalytic system constituted by one or more copper compound(s) and one or more alkali metal and/or alkali-earth metal alkoxide(s), in the presence of one or more solvent(s), the basic features of which are in that to the reaction methanol and one or more alkyl formate(s) are added, with the process being carried out with a concentration of the catalytic system in the solution constituted by the solvents and the same catalytic system, which is comprised within the range of from 0.001 to 1 molar for the compound(s) of copper, and is comprised within the range of from 0.01 to 5 molar for the alkali metal and/or alkali-earth metal alkoxide(s), and at a temperature higher than 40° C., and lower than 200° C.

17 Claims, 4 Drawing Sheets

PROCESS FOR PRODUCING METHANOL FORM SYNTHESIS GAS, IN THE LIQUID PHASE

The present invention relates to a process for the production of methanol from synthesis gas, in the liquid phase.

Methanol, also said "methyl alcohol", whose production at an industrial level was begun several tens of years ago, was always regarded as a valuable intermediate for chemical industry, and was always exploited by being used in such a way.

Its feature, of burning without generating such polluting substances as $NO_x$, $SO_x$ and dusts, when used in steam generators or in gas-powered turbines, and the peculiarity shown by it, of considerably reducing the emissions of CO, when is used in blends with gasoline, render methyl alcohol an "environment-friendly" power source.

Its use as a power source has furthermore a strategic component, in that it makes it possible marginal reserves of natural gas to be exploited, which otherways would remain useless.

The most diffused technologies at an industrial level for methanol production are very similar to one another, and are based all on two basic steps: a first step, in which raw materials are transformed into synthesis gas, and a second step in which $CO/H_2/CO_2$ are converted into methyl alcohol by heterogeneous catalysis, in the gas phase.

The industrial operating conditions for the last-generation copper catalysts are: pressure of from 5 to 10 MPa, temperature of from 230° to 270° C., make-up gas composition: $H_2—CO_2/CO+CO_2=5-8$ (by volume). The relatively low conversion per pass, and therefore the need of keeping a low content of inert gases in the synthesis gas constitute the main limitiations the present technology is subject to.

Catalytic systems have been developed recently, which operate under very mild conditions of temperature and pressure (respectively of 90°-120° C. and 1–5 MPa): in this case, very high CO conversions per pass can be obtained, which can even exceed 90%, thus making it possible the main limitations to the present technology to be overcome to a considerable extent.

In many of these systems, nickel is used as the catalytic metal: some of them operate as slurries (see U.S. Pat. Nos. 4,614,749; 4,619,946; and 4,623,634), other systems operate, on the contrary, under homogeneous catalysis conditions.

Unfortunately, all of these systems suffer from the drawback that under reaction conditions they develop nickel carbonyl, a very toxic compound.

Another system was developed by Mitsui Petrochem. Ind. Ltd., and does not use nickel-based catalysts, but copper-based catalysts (see Japanese patent applications Nos. 110,631/81 and 128,642/82).

The catalytic system of JP-128,642/82 is characterized by the presence of copper compounds, preferably copper alkoxides, copper aryloxides, copper halides, copper carboxylates and copper hydrides, together with alkali-metal alkoxides, preferably sodium methoxide.

Although it displays interesting characteristics, such as the capability of producing methanol under very mild reaction conditions, this catalyst suffers anyway from the drawback that it shows poor productivity rates, which constitutes a limitation from the application standpoint.

The present Applicant has surprisingly found now that the above said catalytic system for producing methanol can operate with decidedly higher activities when specific amounts of methanol and/or of alkyl formate (preferably methyl formate) are added.

In this case, the addition of methanol and/or of alkyl formate favours the obtainment of considerably higher productivity rates, although the process is still carried out under very mild reaction conditions.

The amount of added methanol and/or alkyl formate is strictly correlated to the reaction parameters: copper compound concentration, alkoxide concentration, as well as operating pressure and temperature. When the reaction conditions and the composition of the catalyst are varied, the optimum amount of methanol and/or of alkyl formate varies, which has to be added.

But, when amounts of methanol and/or of alkyl formate are added, which are outside the range according to the present Applicant's correlations, as stated in the following, results are obtained, which may even be negative.

A further, and very important, consequence of the instant, surprising, invention is that, when one turns from a batchwise process to a continuous process, that portion of methanol and/or of alkyl formate, useful for the system to operate at its best, must be recycled.

The precursor of the catalytic system which, together with the added methanol and/or alkyl formate, originates the actual catalytic system for the process for methanol production according to the present invention, is not different from analogous systems as known from the prior art (JP-128,642/82), and is constituted by the combined presence of one or more copper compound(s) of any types, and of one or more alkali-metal and/or alkali-earth-metal alkoxides.

The catalyst can be prepared by mixing the copper compound with the alkoxide, preferably in an organic diluent liquid under reaction conditions.

As the copper compounds useful for the purposes of the present invention, copper carboxylates, such as copper acetate, copper halides, such as copper chloride or copper bromide, copper alkoxides, such as copper-(I) methoxide or copper-(II) methoxide, copper hydride, can be mentioned for merely exemplified purposes.

The alkali-metal alkoxides and/or alkali-earth-metal alkoxides have the formula

$$(RO)_xM$$

wherein M is the alkali or alkali-earth metal, R is an alkyl group of from 1 to 10 carbon atoms, and preferably of from 1 to 5 carbon atoms, x is the valency of the alkali or alkali-earth metal.

A preferred form of said catalytic system is constituted by copper-(I) chloride and sodium methoxide ($CH_3ONa$).

The process for producing methanol from synthesis gas, in the liquid phase, according to the present invention, which comprises reacting CO with $H_2$ in the presence of the hereinabove disclosed catalytic system and in the presence of one or more solvent(s), is characterized in that to the reaction methanol and/or one or more alkyl formate(s) of formula

$$HCOOR_f$$

wherein $R_f$ is an alkyl group containing from 1 to 20 carbon atoms, and preferably from 1 to 10 carbon atoms, and still more preferably 1 carbon atom, are added in such amounts that, in case methanol is added, molar ratios of methanol to copper are obtained, which are comprised within the range of from 1 to 500, and are preferably comprised within the range of from 3 to 30, and molar ratios of alkoxides to methanol are obtained, which are comprised within the range of from 0.05 to 500, and are preferably comprised within the range of from 0.1 to 10, and, in case alkyl formates are added, molar ratios of $HCOOR_f$ to copper are obtained, which are comprised within the range of from 1 to 1000, and are preferably comprised within the range of from 4 to 400, and molar ratios of alkoxides to $HCOOR_f$ are obtained, which are preferably comprised within the range of from 0.05 to 500, and are preferably comprised within the range of from 0.1 to 10, with the process being carried out with a concentration of the catalytic system in the solution constituted by the solvents and by the same catalytic system, which is comprised within the range of from 0.001 to 1 molar, and is preferably comprised within the range of from 0.01 to 0.09, for the compound(s) of copper, and is comprised within the range of from 0.01 to 5 molar, and preferably of from 0.1 to 0.9 molar, for the alkali metal and/or alkali-earth metal alkoxide(s), and at a reaction temperature higher than 40° C., and lower than 200° C., and more preferably comprised within the range of from 60° C. to 150° C.

The partial pressure of the reactants is preferably higher than 1 MPa, and still more preferably, is comprised within the range of from 3 to 5 MPa.

The molar ratio of $H_2/CO$ of the reactant gases is preferably comprised within the range of from 0.5 to 5 and, still more preferably is comprised within the range of from 3 to 5 MPa.

The catalytic system as hereinabove disclosed can operate in a solvent of a simple ether type (such as, e.g.: methyl-tert.-butyl-ether, tetrahydrofuran, n-butyl-ether), of a complex ether type (glycol ethers, such as diglyme or tetraglyme), esters of carboxy acids (such as, e.g., methyl isobutyrate, or $\gamma$-butyrolactone).

Other useful solvents can be sulfones (such as, e.g., sulfolane), sulfoxides (such as, e.g., dimethylsulfoxide), or amines (such as, e.g., pyridine, piperidine, picoline).

The system can operate as well in the presence of high contents (such as, e.g., of percentages of from 30 to 60% by volume) of such inerts as $N_2$ and $CH_4$ in the reaction gas, without the reaction speed being altered, provided that the partial pressure of the reactants is kept at values higher than 1 MPa.

This feature is a very important one, in that it makes it possible a different, and cheaper, technology to be used for prearing the synthesis gas, such as the partial oxidation with atmospheric air.

By operating under those conditions as hereinabove set forth as the preferred conditions, highest conversions of CO per pass of the order of 90%, reaction speeds of about 0.03 $s^{-1}$ (mols of $CH_3OH$ developed per each mol of copper per second) and very high selectivities to methanol (of 80–99%) were obtained, with only dimethylether and methyl formate being obtained as byproducts in noticeable amounts.

BRIEF DESCRIPTION OF THE DRAWINGS

The FIGURES show the rate of production of methanol and methyl formate as a function of reaction time.

Examples are supplied now for the purpose of better illustrating the instant invention, it being anyway understood that said invention is in no way limited to said examples.

EXAMPLE 1

The instant example illustrates the use of the process according to the present invention at 90° C. and under a pressure of 5 MPa in a "batchwise" reactor.

3 mmol of CuCl, 30 mmol of $CH_3ONa$, 50 mmol of methanol and 90 ml of anhydrous tetrahydrofuran are charged to an autoclave equipped with magnetic-drive stirring means and of 300 ml of capacity. The process is carried out under a blanketing nitrogen atmosphere.

The reactor is charged with 1 MPa of an (1:2 by mol) $CO/H_2$ mixture, is heated up to 90° C. and the total pressure inside it is then increased up to 5 MPa with the same gas mixture.

Owing to the reaction, the total pressure tends to decrease during the test; when said total pressure reaches the value of 4 MPa, fresh gas is fed again, in order to increase the pressure back to 5 MPa.

This process is repeated a plurality of times.

By operating in this way, after a 4-hours reaction time, 164 mmol of methanol (including the millimoles of methanol initially charged to the reactor), 43.4 mmol of methyl formate and 0.62 mmol of dimethylether were obtained.

EXAMPLE 2

The instant example shows how a more aimed addition of methanol may yield a still more active catalytic system. The process is carried out under the same experimental conditions as of Example 1, but in this case the added amount of methanol corresponds to 25 mmol.

By operating according to the same methodology as disclosed in Example 1, after a 4-hours reaction time, 276 mmol of methanol (including the millimoles of methanol initially charged to the reactor), 45.4 mmol of methyl formate and 0.25 mmol of dimethylether were obtained.

EXAMPLE 3

The instant example shows how the addition of a larger amount of methanol may yield, on the contrary, a much less active catalytic system. In this case, the added amount of methanol corresponds to 200 mmol.

By still operating under the same conditions, and according to the same methodology, as disclosed in Example 1, after a 4-hours reaction time 219 mmol of methanol (including the millimoles of methanol initially charged to the reactor), 42.7 mmol of methyl formate and 1.24 mmol of dimethylether are obtained.

EXAMPLE 4

Comparative Example

This example shows how in the present invention the addition of methanol leads to the obtainment of a decidedly more active system that the non-promoted system (see the Japanese patent application JP-128,642/82).

The process is carried out in the same way as disclosed in Example 2, with the same catalyst and, obviously, without adding any methanol.

The rate of joint production of methanol and methyl formate according to the present invention as a function of reaction time (line with crosses) is compared in FIG.

1 to the same parameter according to the prior art (line with points).

Figure 1:
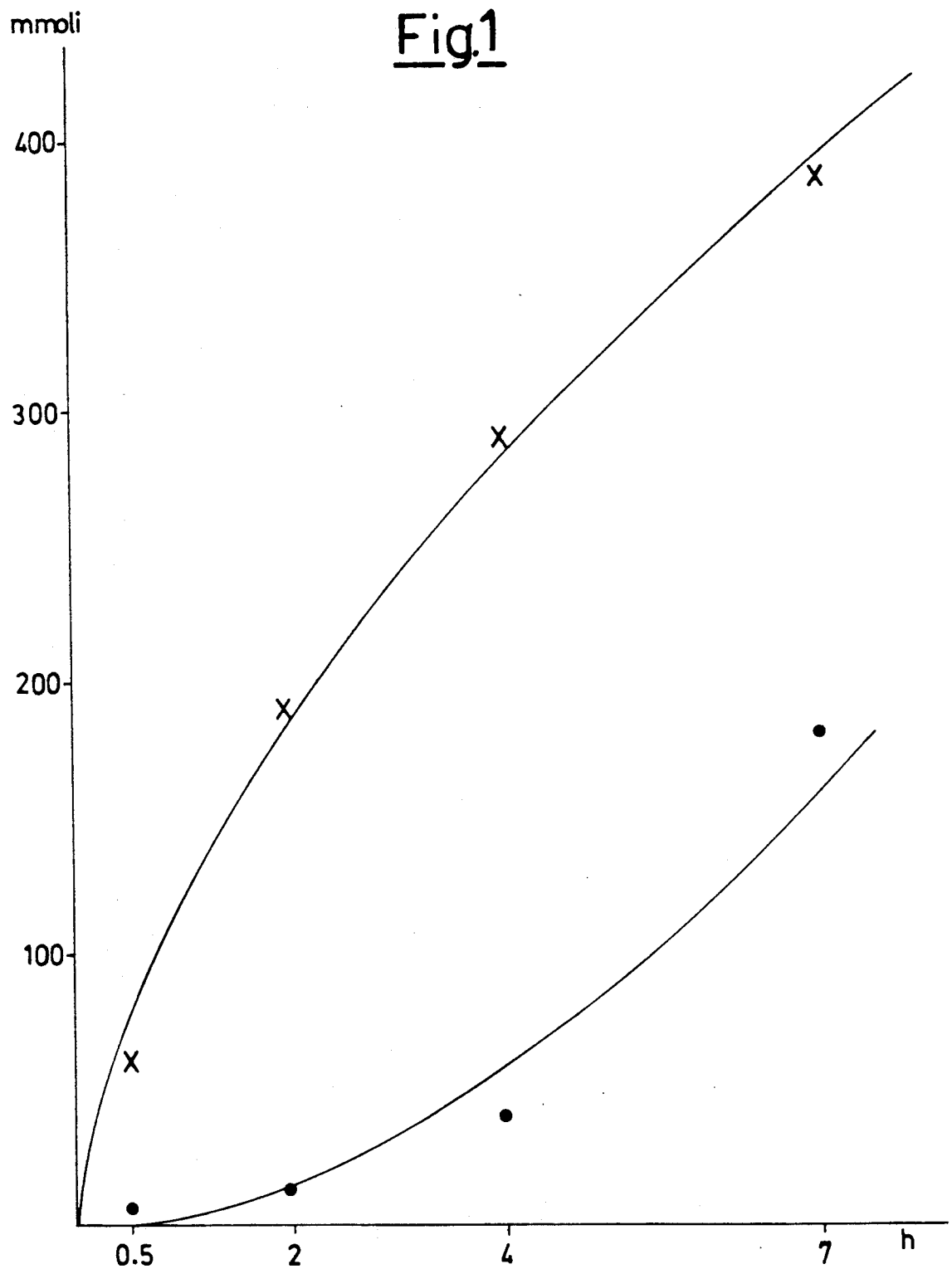

According to the present invention, the amount of 25 mmol of methanol was added, which was subtracted from the actually produced amount of methanol and methyl formate, in order to yield the production values shown in FIG. 1.

EXAMPLE 5

This example shows how the catalytic system is still very active, when methanol is added, even at a temperature different from 90° C.

The reaction is carried out by operating under the same experimental conditions as of Example 1, but in this case the amount of added methanol corresponds to 25 mmol and the reaction temperature is of 60° C.

By still operating according to the same technology as disclosed in Example 1, after a 4-hours reaction time, 123 mmol of methanol (including the millimoles of methanol initially charged to the reactor) and 67.7 mmol of methyl formate are obtained.

EXAMPLE 6

Comparative Example

This example shows how the difference of activity between the present invention with added methanol, and a non-promoted system exists also at different reaction temperatures.

The process is carried out in the same way as disclosed in Example 5, with a reaction temperature of 60° C. and, obviously, without adding any methanol.

Figure 2:
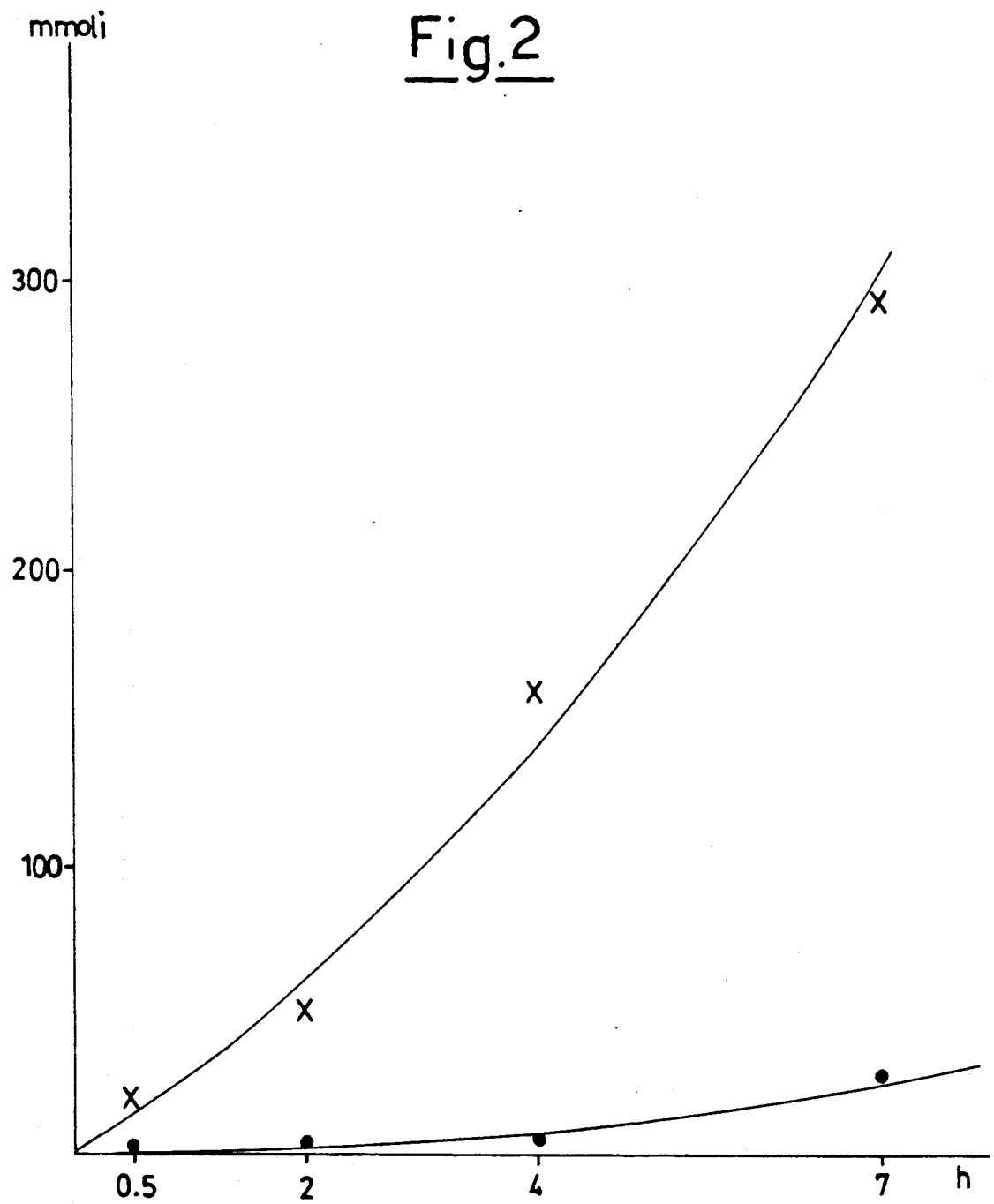

The rate of the production of methanol and methyl formate according to the present invention as a function of reaction time (line with crosses) is compared in FIG. 2 to the same parameter according to the prior art (line with points).

EXAMPLE 7

The instant example illustrates the use of the process according to the present invention at 90° C. and under a pressure of 5 MPa in a "batchwise" reactor, with methyl formate being added instead of methanol.

3 mmol of CuCl, 30 mmol of $CH_3ONa$, 25 mmol of methyl formate and 90 ml of anhydrous tetrahydrofuran are charged to an autoclave equipped with magnetic-drive stirring means and of 300 ml of capacity; the reaction is carried out under a blanketing nitrogen atmosphere.

The reactor is charged with 1 MPa of an (1:2 by mol) $CO/H_2$ mixture, is heated up to 90° C. and the total pressure inside it is then increased up to 5 MPa with the same gas mixture.

Owing to the reaction, the total pressure tends to decrease during the test; when said total pressure reaches the value of 4 MPa, fresh gas is fed again, in order to increase the pressure back to 5 MPa.

This process is repeated a plurality of times.

By operating in this way, after a 4-hours reaction time, 255 mmol of methanol, 43.4 mmol of methyl formate (including the millimoles of methyl formate initially charged to the reactor) and 0.43 mmol of dimethylether were obtained.

Figure 3:
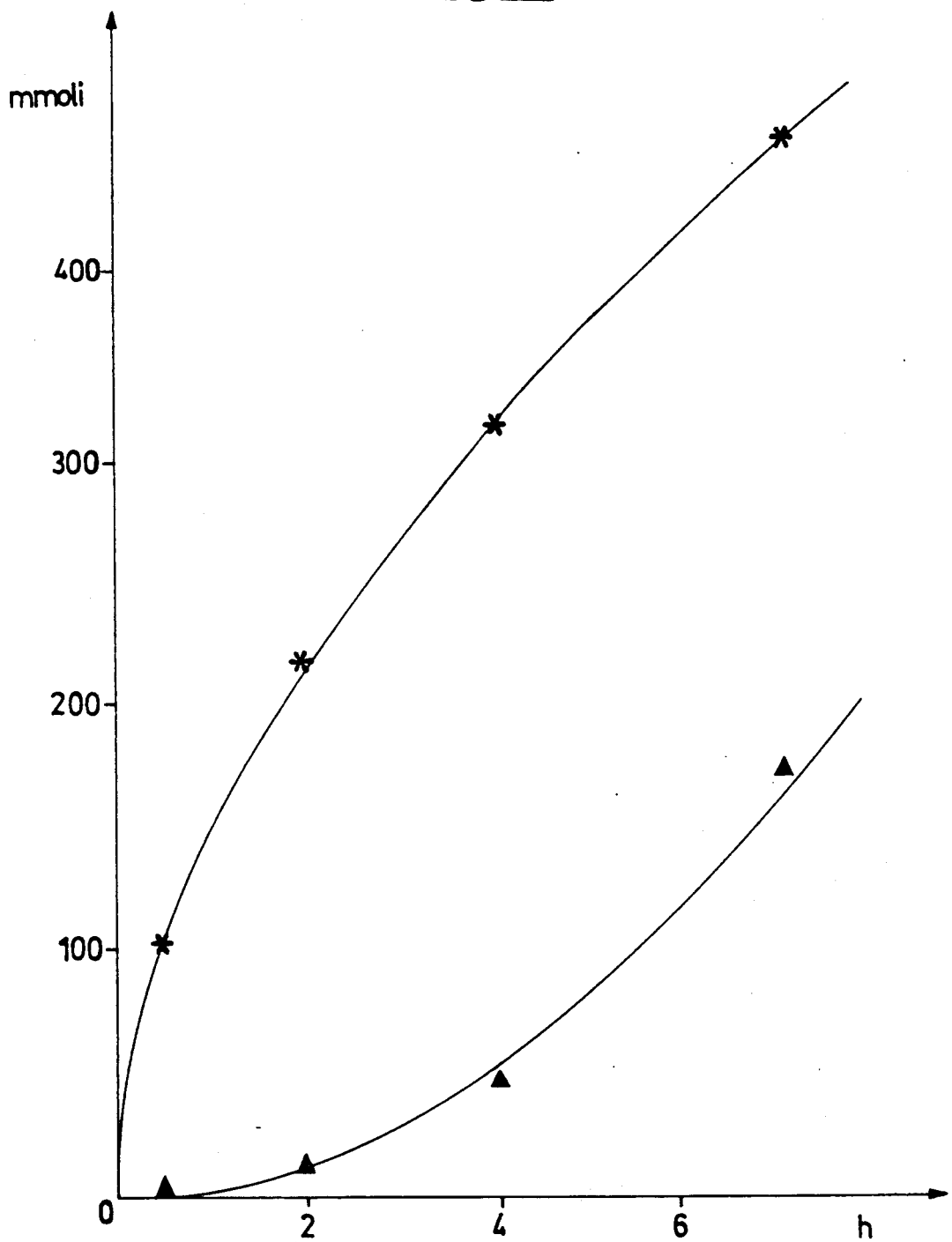

The rate of the joint production of methanol and methyl formate according to the present invention (line with asterisks) as a function of reaction time is compared in FIG. 3 to the same parameter according to the prior art (line with triangles) (see Example 4).

According to the present invention, the amount of 25 mmol of methyl formate was added, which was subtracted from the actually produced amount of methanol and methyl formate, in order to yield the production values shown in FIG. 3.

EXAMPLE 8

This example shows how the catalytic system is still very active, when methyl formate is added, even at a temperature different from 90° C.

The reaction is carried out by operating under the same experimental conditions as of Example 1, but in this case the amount of added methyl formate corresponds to 25 mmol and the reaction temperature is of 60° C.

By still operating according to the same technology as disclosed in Example 1, after a 4-hours reaction time, 172 mmol of methanol and 99.7 mmol of methyl formate (including the millimoles of methyl formate initially charged to the reactor) are obtained.

Figure 4:
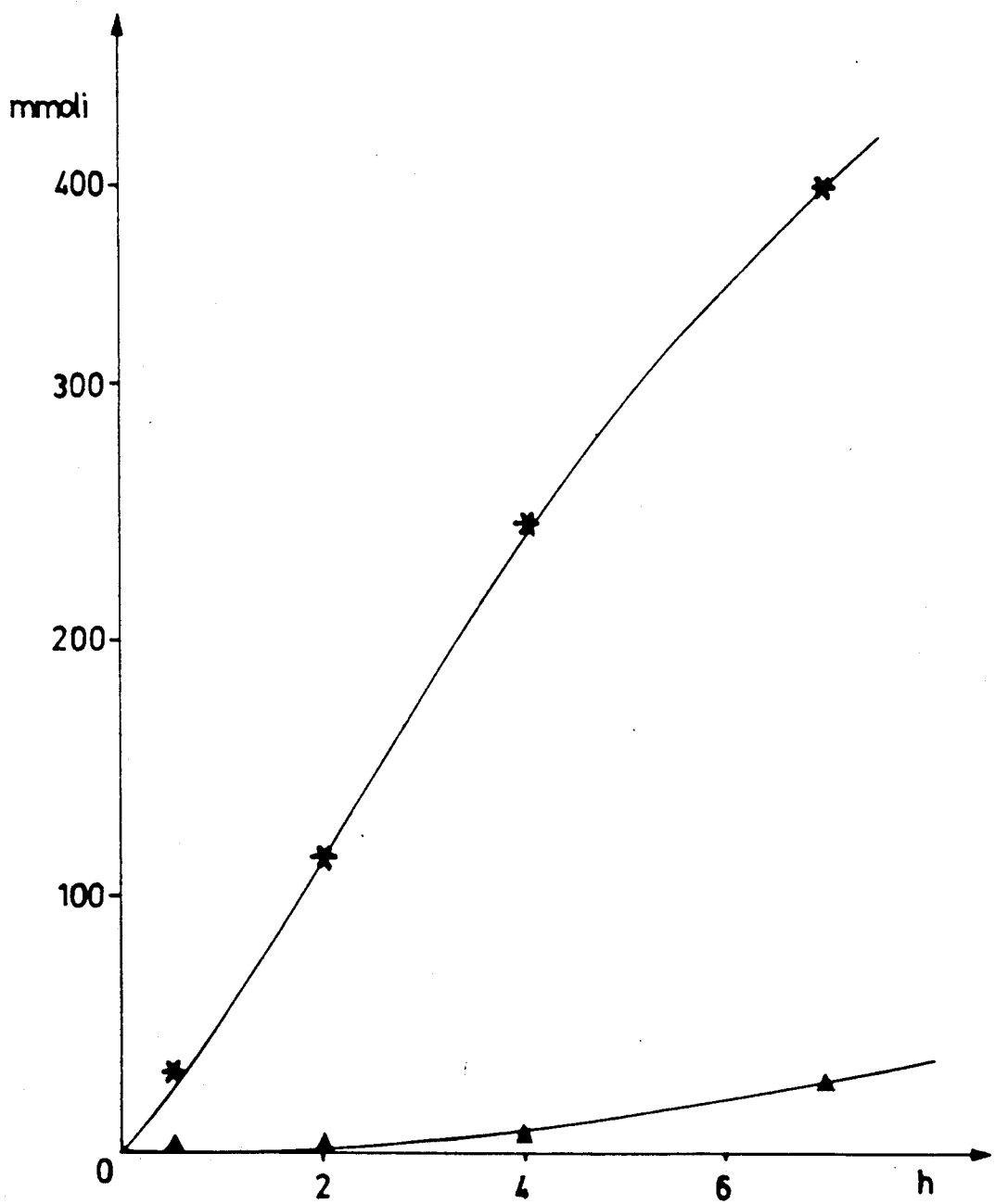

The rate of production of methanol and methyl formate according to the present invention (line with asterisks) as a function of reaction time is compared in FIG. 4 to the same parameter according to the prior art (line with triangles) (see Example 6).

We claim:

1. A process for producing methanol from synthesis gas in the liquid phase, comprising the steps of:

reacting CO and $H_2$, in a molar ratio of 0.5–5, at a temperature higher than 40° C. and lower than 200° C., in the presence of (1) a solution of a solvent and a catalyst system, said catalyst system, comprising a copper compound selected from the group consisting of copper alkoxides, copper halides and copper carboxylates, and an alkali metal alkoxide, alkaline-earth-metal alkoxide or mixture thereof of the formula

$(RO)_xM$ wherein M is an alkali or alkaline-earth metal, R is $C_{1-10}$ alkyl and x is the valence of the alkali or alkaline-earth metal; and (2) methanol, an alkyl formate of the formula

$HCOOR_f$ wherein $R_f$ is a $C_{1-20}$ alkyl group or mixture thereof,
wherein the molar ratio of methanol to copper is 1–500, the molar ratio of said alkali or alkaline-earth metal alkoxide to methanol is 0.05–500, the molar ratio of said alkyl formate to copper is 1–1,000 and the molar ratio of said alkali or alkaline-earth metal alkoxide to said alkyl formate is 0.05–500, and
wherein the concentration of said copper compound in said solution is 0.001–1 molar and the concentration of said alkali or alkaline-earth metal alkoxide in said solution is 0.01–5 molar.

2. The process of claim 1, wherein the concentration of said copper compound in said solution is in the range of 0.01–0.09 molar and the concentration of said alkali or alkaline-earth metal alkoxide in said solution is in the range of 0.1–0.9 molar.

3. The process of claim 1, wherein said reacting step is conducted at a temperature of 60°–150° C.

4. The process of claim 1, wherein said reacting step is conducted at a partial pressure of CO and $H_2$ higher than 1 MPa.

5. The process of claim 4, wherein said reacting step is conducted at a partial pressure in the range of 3-5 MPa.

6. The process of claim 1, wherein said reacting step is conducted in the presence of methanol, wherein the molar ratio of methanol to copper is from 3-30 and the molar ratio of said alkali or alkaline-earth metal alkoxide to methanol is 0.1-10.

7. The process of claim 1, wherein said reacting step is conducted in the presence of said alkyl formate and the molar ratio of said alkyl formate to copper is 4-400 and the molar ratio of said alkoxide to said alkyl formate is 0.1-10.

8. The process of claim 1, wherein $R_f$ is $C_{1-10}$ alkyl.

9. The process of claim 8, wherein $R_f$ is methyl.

10. The process of claim 1, wherein R is $C_{1-5}$ alkyl.

11. The process of claim 1, wherein said reacting step is conducted in the presence of both methanol and said alkyl formate.

12. The process of claim 1, wherein said copper carboxylate is copper acetate.

13. The process of claim 1, wherein said copper halide is copper chloride or copper bromide.

14. The process of claim 1, wherein said copper alkoxide is copper (I) methoxide or copper (II) methoxide.

15. The process of claim 1, wherein said copper compound is copper (I) chloride and said alkali metal alkoxide is sodium methoxide.

16. The process of claim 1, wherein said process is a continuous process.

17. The process of claim 16, wherein said methanol and alkyl formate are continuously recycled to said reacting step.

* * * * *